United States Patent [19]

Bhagwat et al.

[11] Patent Number: 4,996,048

[45] Date of Patent: Feb. 26, 1991

[54] STABILIZING PACKAGED IODOPHOR AND MINIMIZING LEACHING OF IODINE THROUGH PACKAGING

[75] Inventors: Dileep Bhagwat, Peekskill; Oliver Iny, Little Neck; Frank Pedi, Jr., Yorktown Heights, all of N.Y.

[73] Assignee: Euroceltique, S.A., Luxembourg, Luxembourg

[21] Appl. No.: 278,197

[22] Filed: Nov. 30, 1988

[51] Int. Cl.$^5$ .................. A61K 31/79; A01N 59/12; B65D 81/00; B29D 23/00

[52] U.S. Cl. .................. 424/80; 514/967; 523/122; 428/35.5; 428/36.92; 422/37

[58] Field of Search ............ 424/667, 78, 80, 412, 424/413, 414, 415; 523/122; 514/967; 428/35.5, 36.92; 422/37

[56] References Cited

U.S. PATENT DOCUMENTS

| | | | |
|---|---|---|---|
| 2,739,922 | 3/1956 | Shelanski | 452/106 |
| 3,028,300 | 4/1962 | Cantor et al. | 424/80 |
| 3,177,114 | 4/1965 | Cantor et al. | 424/80 |
| 3,898,326 | 8/1975 | Cantor et al. | 424/667 |
| 4,113,857 | 9/1978 | Shetty | 424/80 |
| 4,322,003 | 3/1982 | Long | 428/458 |
| 4,384,960 | 5/1983 | Polley | 424/667 |
| 4,526,751 | 7/1985 | Gartner | 424/80 |
| 4,575,491 | 3/1986 | Pollack et al. | 424/80 |
| 4,584,192 | 4/1986 | Dell et al. | 424/667 |
| 4,666,706 | 5/1987 | Farquharson | 424/412 |
| 4,668,510 | 3/1987 | Shetty | 424/78 |

FOREIGN PATENT DOCUMENTS

| | | | |
|---|---|---|---|
| 8201469 | 5/1982 | PCT Int'l Appl. | 424/414 |
| 993319 | 5/1965 | United Kingdom . | |

*Primary Examiner*—Johnnie R. Brown
*Assistant Examiner*—Carmen Pili-Curtis
*Attorney, Agent, or Firm*—Steinberg and Raskin

[57] ABSTRACT

Minimizing the leaching of iodine through packaging containing organic iodophor solution, by introducing into the packaging an amount of additional iodide which minimizes leaching of the iodine through the packaging and stabilizes the iodophor solution therein. The iodophor is preferably polyvinylpyrrolidone iodine.

14 Claims, No Drawings

STABILIZING PACKAGED IODOPHOR AND MINIMIZING LEACHING OF IODINE THROUGH PACKAGING

BACKGROUND OF THE INVENTION

The present invention is directed to minimizing loss of iodine from an iodophor solution, notably polyvinylpyrrolidone iodophor, which is stored within a packaging. More specifically, the present invention is directed to a method for minimizing this loss, and to the packaging provided therefor, in which a certain minimal level of additional iodide is provided, in addition to the iodophor solution, which prevents or minimizes leaching of iodine through the packaging itself.

Combination of elemental iodine and certain organic polymers, e.g., polyvinylpyrrolidone and detergent polymers, have been termed iodophors. The organic polymers used to form an iodophor comprise a broad range in molecular weight and chain length, and may be either ionic or non-ionic in character, as well as possessing either surfactant or non-surfactant properties. A loose bond forms between the iodine and organic polymer to form a complex. Aqueous solutions of up to about 30% in iodine content, may be prepared.

The general method for the preparation of a iodophor complex is to bring into intimate contact, elemental diatomic iodine with the selected polymer, either in the dry or powder form or in the presence of a suitable solvent. Heat may be used to accelerate complex formation. Upon completion of the reaction, the iodophor complex of the respective polymeric carrier with iodine is obtained in certain reproducible proportions of one to the other.

Iodophor preparations are described in terms of available or titratable iodine which is considered to be the iodine released from the complex to exert germicidal action thereof. However, such available iodine determinations do not reflect either the total iodine content of the iodophor, or its germicidal potency. The iodine moiety of polyvinylpyrrolidone (povidone)-iodine complex is present in an aqueous iodophor solution in the form of different thermodynamically stable anionic iodine species and diatomic iodine. The anionic iodine forms are capable of generating diatomic iodine in the course of their respective equilibrium reactions. The anionic species do not distribute themselves into an extracting solvent which removes only the nonionic iodine. Such iodine is generated in the course of the iodine equilibrium reaction and extraction thereof by a solvent fractionates the equilibrium state. The disturbed equilibrium reaction is soon re-established to restore new anionic iodine species, but now at a different concentration level since the previous aqueous iodine content of the solution has been reduced by the extracting solvent.

Since the iodophor iodine exerting microbicidal action exists in solution in dynamic equilibrium with ionic iodine species, removal of one or more of the iodine species results in formation of new equilibrium forms. An extracting solvent removes or consumes iodine from the iodophor solution in a manner similar to that of a microbial and organic load during degerming use of the iodophor solution. The amount of iodine available for germicidal action in an iodophor preparation therefore is the amount of iodine in equilibrium in the solution at the time of use. Such equilibrium iodine content represents the germicidal potency of the preparation, but not the total iodine content titrated for the preparation nor the apparent distribution of the iodine forms. Although iodophor solutions have been assayed in the art for available or titratable iodine, it is the equilibrium iodine which is the particular form of iodine present in the iodophor solution that is instantly available to exert microbicidal action. This form of iodine differs from titratable iodine and the other iodine species present in the iodophor solution. Therefore, the equilibrium iodine content of an iodophor solution is to be distinguished from its titratable iodine content.

The titratable iodine content of an iodophor preparation includes the iodine reservoir of the iodophor preparation (povidone iodine), as well as the equilibrium iodine in solution:

Titratable iodine = Reservoir Iodine + Equilibrium Iodine

However, it is the equilibrium iodine alone that exerts the microbicidal action of the preparation at any given moment. The portion of the titratable iodine content remaining after subtracting the amount of equilibrium iodine present, serves as the iodine reservoir to generate new equilibrium iodine in solution as it is consumed by the microbial and bio-organic load in the course of microbicidal activity, but does not exert such germicidal action by itself.

Povidone-iodine (polyvinylpyrrolidone-iodine or PVP-I) USP (U.S. Pharmacopeia) is the raw material used in the preparation of all PVP-I containing formulations. Povidone-iodine is a complex of iodine with povidone. It contains not less than 9.0% by weight, and not more than 12% by weight of available-iodine (titratable iodine) calculated on a dry basis. Povidone Iodine USP has a specification for iodide ion of not more than 6.6% by weight on a dry basis.

The level of iodide ions inherently present in any PVP-I formulation using PVP-I raw material, therefore depends on the amount of iodide ion present in the raw material PVP-I used. For example, on a theoretical basis, if the PVP-I contains 6% by weight iodide ion, then a formulation containing 10% by weight of PVP-I would contain 0.6% by weight iodide ion. However, PVP-I raw material containing a level of iodide ion greater than specifications of the U.S. Pharmacopeia, could also be used in formulating a PVP-I containing product.

Thus, the minimum amount of iodide ion inherently present in a PVP-I formulation could be as low as 0.0% by weight, while the maximum amount of iodide ion inherently present in such a PVP-I formulation would be the amount contributed by the PVP-I raw material used to formulate the same. For example, on a theoretical basis, if a formulation contains 0.36% by weight PVP-I, and the PVP-I contains the maximum iodide allowable of 6.6% by weight, then the formulation will have 0.0237% by weight iodide present.

Iodophor solutions, notably povidone-iodine, have been packaged for medicinal use, e.g. in soft plastic bottles or containers which can be used for various medicinal purposes, e.g. douching. However, a severe problem that has been encountered with such packaged iodophor solutions, is that elemental iodine (equilibrium iodine) has leached through the packaging itself. This has resulted both in a decrease in stability and medicinal capacity of the iodophor solution contained within the packaging, and has also made it difficult to handle such packaging since the elemental iodine which has leached therethrough causes staining and burning if touched.

However, it has now been surprisingly found that separate introduction of additional iodide, above and apart from the iodide already present in the noted iodophor solution, actually reduces and even totally eliminates the leaching of any elemental iodine from the iodophor solution through the packaging.

SUMMARY OF THE INVENTION

Accordingly, it is an object of the present invention to improve the packaged stability of iodophor solutions, such as povidone-iodine.

It is also an object of the present invention to reduce and even totally eliminate possibility of iodine leaching from a packaged iodophor solution, through the packaging thereof.

It is another object of the present invention to maintain the medicinal capacity of iodophor solution that has been packaged, especially in a plastic container or packaging.

It is an additional object of the present invention to reduce and even totally eliminate detrimental effects such as decrease in stability and medicinal capacity, which occur when iodine leaches through packaging containing an iodophor solution of the same, which might also cause staining and/or burning when touched.

These and other objects are attained by the present invention which is directed to a packaging containing organic iodophor solution, and an amount of additional iodide which improves the stability of the iodophor and minimizes leaching of iodine through the packaging. The iodophor is preferably polyvinyl pyrrolidone iodophor. The packaging is preferably formed from polyethylene, and is preferably a sealed plastic container, e.g. a squeezable plastic douche bottle.

Preferably, at least about 0.01% by weight of the additional iodide, based on the iodophor solution, is introduced into the packaging. The packaging preferably contains up to about 4.0% of the additional iodide, more preferably up to about 1.5% of the additional iodide, and most preferably up to about 1.0% of the additional iodide, based on the iodophor solution. The packaging also preferably contains at least about 0.02% of the additional iodide, and more preferably at least about 0.07% of the additional iodide, based on the iodophor solution.

The iodophor solution itself preferably comprises about 0.01%-0.03% of iodide therein, in addition to the additional amount of iodide that has been introduced, with this additional iodide preferably being KI.

Furthermore, the present invention is also directed to a method for improving the stability of the iodophor and minimizing leaching of iodine from iodophor solution through packaging containing the same, which comprises introducing, into the packaging, an additional amount of iodide which improves the stability of the iodophor and minimizes leaching of iodine through the packaging.

DESCRIPTION OF THE PREFERRED EMBODIMENTS

A conventional iodophor preparation, e.g. the povidone-iodine, can be prepared in a conventional manner outlined in the Background portion of the present case, and can then be introduced in any convenient manner into the appropriate packaging. The minimum amount of additional iodide (e.g. potassium iodide) for example, which must be added to such a formulation is most preferably about 0.076% by weight, based on the iodophor solution itself, while the maximum amount of additional iodide to be added to such a formulation is dictated by the nature of the formulation itself and packaging. In any event, preferably up to a maximum of about 1.5% by weight iodide, based on the iodophor solution, may be added into the packaging itself.

The preferred amount of iodide added to the noted iodophor formulation, depends on the nature of the formulation and on the packaging. For example, an optimal amount of additional iodide to be added would provide a formulation containing about 0.36% PVP-I and about 0.91% weight/volume iodide when the formulation is packaged in a low density, polyethylene packaging (all percents are used herein are weight-/volume unless otherwise noted). This particular formulation results in the desired stability, as documented in Table X below (Example I2). The 3 Mo/40° C. data in Table X shows that for Examples 12, 13 and 14, the percent available iodine shows acceptable stability, while Examples 10 and 11 do not show as good stability. However, the same formulation in a different package may require a different, preferred level of iodide.

The present invention is applicable to all halophors, including iodophors, with the iodophors being any iodine-releasing material, including surfactant-iodophors. While PVP-I is the preferred iodophor, the present invention is applicable to any iodine-releasing material. For example, other iodophor complexes comprise non-ionic, cationic and anionic detergent carriers. An iodophor compound may be prepared with a commercially available non-ionic surface active agent as for example, the liquid non-ionic polyglycol ether type surface active agents which are obtained by condensing alkylene oxides with water-insoluble organic compounds containing at least six carbon atoms and having an active hydrogen, such as organic hydroxy compounds, i.e., alcohols, phenols, thiophene, primary and secondary amines, carboxylic and sulfonic acids and their amides. Non-ionic polyglycol ether type surface active agents of this class are well known in the art and are disclosed, together with methods for their preparation in U.S. Pat. Nos. 1,970,578 and 2,213,477. These agents may be represented by the general formula:

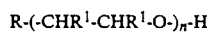

$$R\text{-}(\text{-}CHR^1\text{-}CHR^1\text{-}O\text{-})_n\text{-}H$$

wherein R represents the residue of organic compound containing an active hydrogen, $R^1$ represents hydrogen or lower alkyl and 'n' represents an interger of from 3 to 100 or higher, but usually from 6 to 50. These compounds are readily obtained by the methods disclosed in the above cited U.S. Pat. Nos. 1,970,578 and 2,213,477 by condensing a polyglycol ether containing the required number of alkyleneoxy groups, or an alkylene oxide, usually ethylene oxide, propylene oxide or butylene oxide, with a water-insoluble organic compound containing at least 6 carbon atoms and having an active hydrogen, as for example an alkylphenol.

Other members of the group of non-ionic surfactants also may be used to prepare iodophors as, for example, the class of non-ionic surfactants characterized by the condensation of polyoxypropylene glycol with ethylene oxide containing various chain lengths. Such non-ionic agents are disclosed and claimed in U.S. Pat. No. 2,674,619 and have the general formula:

$$HO\text{-}(C_2H_4O)_x(C_3H_6)_y(C_2H_4O)_zH$$

wherein Y equals at least 15; and $(C_2H_4)$ $z+z$, equals 20–90 percent of the total weight of the compound. These non-ionic surfaces active agents are available commercially and known by the trade name Pluronics, a product of Wyandotte Chemicals Corporation of Wyandotte, Mich. and for purposes of brevity these non-ionic compounds will hereinafter be referred to as Pluronics.

A suitable non-ionic surfactant iodophor complex may be prepared by dissolving in acidified water a sufficient quantity, as for example, between 90 and 99 percent by weight, of the selected non-ionic surface active agent as for example, octylphenoxypoly-(ethleneoxy) ethanol, wherein R is an octylphenoxy group, R' is a hydrogen and n is nine, and adding from 1 to 12 grams of iodide ion obtained from a soluble iodide salt including hydriodic acid, and from 0.1 to 1.0 percent by weight of iodate ion, all the while maintaining the pH of the solution to be below pH 3. A strong brown color instantly develops as the exothermic reaction proceeds and the mixture is stirred while the pH is monitored and adding small increments of the iodate ion until there is no longer any iodide ion available upon assay. Stirring is continued for at least one hour, after which the solvent is evaporated.

In place of octylphenoxypoly-(ethyleneoxy) ethanol described above, there may be substituted other members of this class of non-ionic detergents as for example, nonylphenoxypoly (ethyleneoxy) ethanol.

It has also been found that anionic iodine complexed may also be prepared utilizing members of the group of anionic surface active agents represented by the formula:

$$R\text{-}NR'\text{-}CH_2\text{-}CHx\text{-}SO_3\text{-}Y$$

wherein R is the radical $CxH$ $(2x+1)$ $CO$; x being an integer of from 5 to 17, R being selected from group consisting of hydrogen, $(C_1\text{-}C_4)$ alkyl and cyclohexyl radicals and Y being selected from the group consisting of salt-forming cations. The preferred anionic detergent compounds are of the well known groups of anionic surface active agents known as alkanoyl taurates and alkylaryl sulfonate such as alkyl benzene sodium sulfonate and alkyl naphthyl sodium sulfonate.

When it is desired to utilize anionic detergent agents as a carrier for iodine in the preparation of iodophors, then from 90 to 99 percent by weight of the selected anionic iodine carrier is mixed with from 1 to 10 percent by weight of iodide ion and the whole is dissolved in acidulated water. Then, from 0.1 to 1.0 percent of an iodate ion is added slowly until no further iodide ion is present in the solution upon testing. The solvent is evaporated to recover the formed iodophor complex in a substantially pure form.

When a cationic detergent iodophor is desired as the iodine carrier, then the well known cationic surfactant compounds as for example, the quaternary ammonium salts such as those formed by the alkylation of fatty amines; straight-chain fatty amine salts having from 8 to 18 carbon atoms in chain length, as for example, octadecyl maine; amino amides and imidazolines may be used. The manufacturing process as described above is used to result in a superior iodophor preparation than was hitherto known after the methods described in the prior art.

When a cationic detergent iodophor is to be prepared, then the same ratios of reagents are used, that is from 90 to 99 percent by weight of the selected cationic detergent compound is dissolved in acidulated aqueous solution and from 1 to 10 percent by weight of iodide ion is added together with from 0.01 to 1.0 percent of iodate ion. The mixture is stirred until no iodide ion is evident upon testing. The formed cationic detergent iodophor is recovered in a substantially pure form and exhibits an extraordinary stability.

The amount of iodide present in iodophor formulations comes from the inherent quantity of iodide present in the iodophors. The minimum amount of additional iodide (e.g. potassium iodide) which must be added to such an iodophor formulation, is preferably about 0.0765%, based on the overall iodophor solution, while a maximum amount of additional iodide which should be added to such a formulation, and is dictated by the nature of the formulation and the packaging, is preferably up to about 1.5% based on the iodophor preparation.

A preferred amount of iodide to be added to a formulation naturally depends on the nature of the formulation and the packaging component, as noted above. An amount of iodide that gives the optimal desired characteristics (stability) in a formulation for a particular packaging component, is the goal. A preferred amount of added iodide preferably lies in the range of about 0.076% to 1.5%, depending upon the packaging.

Examples of iodide, salts which can be added to such iodophor preparations, include sodium iodide, potassium iodide, calcium iodide, and zinc iodide, with potassium iodide specifically being preferred. The present invention is extremely effective with all kinds of packaging that has been used to contain PVP-I formulations, i.e. most types of plastic materials which are permeable to iodine, such as low density polyethylene, high density polyethylene, etc. The loss of iodine is a function of the type of plastic, wall thickness of the container thereof, and also of the temperature.

The iodophor preparation with the additional iodide may be prepared in the following manner:
(i) In a suitable stainless steel tank, purified water representing approximately 90% of the purified water required for the batch is collected. Mechanical agitation; is started
(ii) The iodophor (povidone-iodine) powder is added into the vortex created by the mixer;
(iii) In a separate stainless steel container the additional iodide (as the salt, such as potassium or sodium salt) is dissolved in purified water representing approximately 5% of the total batch volume. This solution is added to the batch and mixed;
(iv) Surfactant is slowly added to the batch and mixed;
(v) Enough purified water to bring the batch to 98% of final volume is added. Fragance, if any is added, and mixed;
(vi) pH of the batch is adjusted to the desired pH. A solution of 5% sodium hydroxide is used to adjust the pH when below the target pH. A solution of diluted hydrochloric acid is used the adjust to pH when above the target pH; and
(vii) Sufficient purified water is added to bring the batch to final volume and mixed, followed by packaging into containers.

Variations of this procedure would also accomplish the same results. For example, the iodide could be added at any stage of the manufacturing process, such as (1) before the povidone-iodine, (2) with the povidone-iodine as a powder or solution, or (3) after the addition of the surfactant and fragance. The additional iodide could alternately be added to the iodophor raw material during manufacture or after manufacture.

The present invention will be described in greater detail below, with reference to the following examples which have been conducted to illustrate the present invention, and to which the present invention is not, however, intended to be limited to the specific details thereof. In these examples, all ingredients are commercially available and the compositions were all prepared as noted above, with the stability of the product assessed by monitoring the percent by weight/volume available iodine over time, at a particular temperature and for a particular packaging. The % available iodine was determined by the method described in U.S. Pharmacopeia XXI under povidone iodine topical solution (page 864). The sample size was increased to 50 ml. with appropriate correction in the calculations when dilute solutions were assayed. All plastic packaging components had wall thickness in the range of about 0.030 inches, plus/minus 0.012 inches.

EXAMPLE I

| Ingredient | % w/v |
|---|---|
| PVP-I | 0.5 (0.5 g in 100 ml of the formula) |
| Surfactant | 0.004 |
| Fragrance | 0.01 |
| Purified Water qs ad | 100 |
| Iodide present in the iodophor solution was about 0.025%. | |
| No additional Iodide was added. | |

The resulting solution was examined for stability in the following packaging at 40° C.:
1. Low Density Polyethylene (LDPE)
2. High Density Polyethylene (HDPE)
3. Glass The stability profiles are presented in Table I

TABLE I
STABILITY PROFILE OF EXAMPLE 1 IN LDPE, HDPE AND GLASS AT 40° C.

| TIME | % Available Iodine | | |
|---|---|---|---|
| | LDPE | HDPE | GLASS |
| Initial | 0.048 | 0.048 | 0.048 |
| 1 Month/40° C. | 0.023 | 0.034 | 0.041 |
| 2 Months/40° C. | 0.015 | 0.025 | 0.041 |
| 3 Months/40° C. | 0.007 | 0.023 | 0.040 |

As can be observed, the stability of the product is a function of the packaging at a given temperature.

The present invention will demonstrate, as documented below, that stability (even in one of the the worst situations when packaged in Low Density Polyethylene) can be greatly improved when an additional amount of Iodide is included in the formula.

EXAMPLE 2

| Ingredient | % w/v |
|---|---|
| PVP-I | 0.6 |
| Surfactant | 0.004 |
| Fragrance | 0.004 |
| Purified water qs ad | 100 |
| Iodide present in the iodophor solution was about 0.03%. | |
| No additional Iodide was added. | |

The resulting solution was examined for stability in bottles made of 60% High Density Polyethylene and 40% Low Density Polyethylene.

The stability profile at 40° C. is presented in Table II:

TABLE II
STABILITY PROFILE OF EXAMPLE 2 IN A PACKAGE CONTAINING 60% HDPE AND 40% LDPE

| TIME | % Available Iodine |
|---|---|
| Initial | 0.060 |
| 1 Month/40° C. | 0.041 |
| 2 Months/40° C. | 0.025 |
| 3 Months/40° C. | 0.024 |

The stability in a package containing 60% HDPE and 40% LDPE is better than when packaged in 100% LDPE, but not as good as when packaged in 100% HDPE (Example 1).

EXAMPLE 3

| Ingredient | % w/v |
|---|---|
| PVP-I | 0.6 |
| Surfactant | 0.004 |
| Fragrance | 0.004 |
| Iodide | 0.076 |
| Purified Water qs ad | 100 |

Iodide present in the iodophor solution was about 0.03%. Added Iodide was 0.076%

The resulting solution was examined for stability in the following containers at 40° C.:
1. Glass
2. High Density Polyethylene
3. Low Density Polyethylene coated with Polyvinyl Alcohol
4. Low Density Polyethylene coated with Polyvinylidine Chloride
5. Fluorinated Low Density Polyethylene bottle (#8187-95); LDPE Bottle with Fluorine modified surface in contact with the Product)
6. Fluorinated Low Density Polyethylene bottle (#8187-96; LDPE Bottle with a specially treated experimental gas formulation)

The stability profiles at 40° C. are presented in Table III:

TABLE III
STABILITY PROFILE OF EXAMPLE 3 IN LDPE, HDPE AND GLASS AT 40° C.

| | % Available Iodine | | | | | |
|---|---|---|---|---|---|---|
| | Package # | | | | | |
| TIME | 1 | 2 | 3 | 4 | 5 | 6 |
| Initial | 0.06 | 0.06 | 0.06 | 0.06 | 0.06 | 0.06 |
| 1 Month/40° C. | 0.057 | 0.053 | 0.041 | 0.046 | 0.042 | 0.051 |
| 2 Months/40° C. | 0.057 | 0.050 | 0.033 | 0.038 | 0.033 | 0.045 |
| 3 Months/40° C. | 0.057 | 0.047 | 0.028 | 0.023 | 0.027 | 0.043 |

EXAMPLE 4

| Ingredient | % w/v |
|---|---|
| PVP-I | 0.36 |
| Surfactant | 0.004 |
| Fragrance | 0.004 |
| Purified Water qs ad | 100 |

Iodide present in the iodophor solution was about 0.018%. No additional Iodide was added.

The resulting solution was examined for stability in the following packages at 40° C.

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

"Form-fill seal bottles" are plastic containers which are manufactured from a thermoplastic granulate, filled, and sealed in the same automatic machine. In operation, a plastic tube is extruded from melted plastic granulate. Then, by a plastic forming process called blow-molding, compressed air is blown into the tube, pushing out the warm plastic walls until they conform to the shape of a surrounding mold. A metered amount of product is introduced into the formed container. The container is sealed, the mold opens and the finished, filled container is released on to a conveyor.

"Natural" polyethylene contains no added pigment. The "White" polyethylene contains a pigment (such as Titanium Dioxide) to render the plastic white.

The stability profiles at 40° C. are presented in Table IV:

TABLE IV
STABILITY PROFILE OF EXAMPLE 4 IN LDPE, HDPE AND GLASS AT 40° C.
% Available Iodine

| TIME | Package # | | | | |
|---|---|---|---|---|---|
| | 1 | 2 | 3 | 4 | 5 |
| Initial | 0.036 | 0.036 | 0.036 | 0.036 | 0.036 |
| 1 Month/40° C. | 0.036 | 0.016 | 0.008 | 0.027 | 0.027 |
| 2 Months/40° C. | 0.035 | 0.009 | 0.007 | 0.022 | 0.022 |
| 3 Months/40° C. | 0.034 | 0.002 | 0.005 | 0.018 | 0.020 |

EXAMPLE 5

| Ingredient | % w/v |
|---|---|
| PVP-I | 0.36 |
| Surfactant | 0.004 |
| Fragrance | 0.004 |
| Iodide | 0.15 |
| Purified Water qs ad | 100 |

Iodide present in the Iodophor solution was about 0.018%. Added Iodide was 0.15%.

The resulting solution was examined for stability in the following packages at 40° C.:

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

The stability profiles at 40° C. are presented in Table V:

TABLE V
STABILITY PROFILE OF EXAMPLE 5 IN LDPE, HDPE AND GLASS AT 40° C.
% Available Iodine

| TIME | Package # | | | | |
|---|---|---|---|---|---|
| | 1 | 2 | 3 | 4 | 5 |
| Initial | 0.036 | 0.036 | 0.036 | 0.036 | 0.036 |
| 1 Month/40° C. | 0.036 | 0.031 | 0.029 | 0.033 | 0.033 |
| 2 Months/40° C. | 0.035 | 0.028 | 0.024 | 0.031 | 0.031 |
| 3 Months/40° C. | 0.034 | 0.025 | 0.020 | 0.031 | 0.031 |

EXAMPLE 6

| Ingredient | % w/v |
|---|---|
| PVP-I | 0.36 |
| Surfactant | 0.004 |
| Fragrance | 0.004 |
| Iodide | 0.228 |
| Purified Water qs ad | 100 |

Iodide present in the Iodophor solution was about 0.018%. Added Iodide was 0.228%.

The resulting solution was examined for stability in the following packages at 40° C.:

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

The stability profiles at 40° C. are presented in Table VI:

TABLE VI
STABILITY PROFILE OF EXAMPLE 6 IN LDPE, HDPE AND GLASS AT 40° C.
% Available Iodine

| TIME | Package # | | | | |
|---|---|---|---|---|---|
| | 1 | 2 | 3 | 4 | 5 |
| Initial | 0.036 | 0.036 | 0.036 | 0.036 | 0.036 |
| 1 Month/40° C. | 0.036 | 0.033 | 0.031 | 0.034 | 0.034 |
| 2 Months/40° C. | 0.036 | 0.030 | 0.028 | 0.033 | 0.033 |
| 3 Months/40° C. | 0.034 | 0.028 | 0.022 | 0.0325 | 0.032 |

EXAMPLE 7

| Ingredient | % w/v |
|---|---|
| PVP-I | 0.036 |
| Surfactant | 0.004 |
| Fragrance | 0.004 |
| Iodide | 0.342 |

| Ingredient | % w/v |
|---|---|
| Purified Water qs ad | 100 |

Iodide present in the Iodophor solution was about 0.018%. Added Iodide was 0.342%.

The resulting solution was examined for stability in the following packages at 40° C.

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

The stability profiles at 40° C. are presented in Table VII:

TABLE VII

STABILITY PROFILE OF EXAMPLE 7 IN LDPE, HDPE AND GLASS AT 40° C.

Available Iodine

| TIME | Package # | | | | |
|---|---|---|---|---|---|
| | 1 | 2 | 3 | 4 | 5 |
| Initial | 0.036 | 0.036 | 0.036 | 0.036 | 0.036 |
| 1 Month/40° C. | 0.036 | 0.034 | 0.034 | 0.035 | 0.033 |
| 2 Months/40° C. | 0.036 | 0.032 | 0.029 | 0.034 | 0.034 |
| 3 Months/40° C. | 0.035 | 0.031 | 0.026 | 0.034 | 0.0335 |

EXAMPLE 8

| Ingredient | % w/v |
|---|---|
| PVP-I | 0.45 |
| Surfactant | 0.004 |
| Fragrance | 0.004 |
| Iodide | 0.285 |
| Purified Water qs ad | 100 |

Iodide present in the Iodophor solution was about 0.023%. Added Iodide was 0.285%.

The resulting solution was examined for stability in the following packages at 40° C.

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

The stability profiles at 40° C. are presented in Table VIII.

TABLE VIII

STABILITY PROFILE OF EXAMPLE 8 IN LDPE, HDPE AND GLASS AT 40° C.

% Available Iodine

| TIME | Package # | | | | |
|---|---|---|---|---|---|
| | 1 | 2 | 3 | 4 | 5 |
| Initial | 0.045 | 0.045 | 0.045 | 0.045 | 0.045 |
| 1 Month/40° C. | 0.045 | 0.043 | 0.041 | 0.044 | 0.043 |
| 2 Months/40° C. | 0.041 | 0.041 | 0.041 | 0.042 | 0.042 |
| 3 Months/40° C. | 0.043 | 0.038 | 0.038 | 0.0416 | 0.041 |

EXAMPLE 9

| Ingredient | % w/v |
|---|---|
| PVP-I | 0.45 |
| Surfactant | 0.004 |
| Fragrance | 0.004 |
| Iodide | 0.426 |
| Purified Water qs ad | 100 |

Iodide present in the Iodophor solution was about 0.022%. Added Iodide was 0.42%.

The resulting solution was examined for stability in the following packages at 40° C.:

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

The stability profiles at 40° C. are presented in Table IX:

TABLE IX

STABILITY PROFILE OF EXAMPLE 9 IN LDPE, HDPE AND GLASS AT 40° C.

% Available Iodine

| TIME | Package # | | | | |
|---|---|---|---|---|---|
| | 1 | 2 | 3 | 4 | 5 |
| Initial | 0.045 | 0.045 | 0.045 | 0.045 | 0.045 |
| 1 Month/40° C. | 0.045 | 0.043 | 0.042 | 0.044 | 0.044 |
| 2 Months/40° C. | 0.044 | 0.041 | 0.040 | 0.043 | 0.043 |
| 3 Months/40° C. | 0.043 | 0.040 | 0.036 | 0.0426 | 0.042 |

EXAMPLE 10

| Ingredient | % w/v |
|---|---|
| PVP-I | 0.36 |
| Surfactant | 0.004 |
| Fragrance | 0.004 |
| Iodide | 0.61 |
| Purified Water qs ad | 100 |

Iodide present in the Iodophor solution was about 0.018%. Added Iodide was 0.61%.

The resulting solution was examined for stability in Low Density Polyethylene and glass at 40° C. and Room Temperature. A comparative stability Table of Example 10 to Example 14 is presented after the Example 14 formula in Tables X and XI.

This series of examples demonstrates the effects of increasing amounts of Iodide on the stability in the same package.

EXAMPLE 11

| Ingredient | % w/v |
|---|---|
| PVP-I | 0.36 |
| Surfactant | 0.004 |
| Fragrance | 0.004 |
| Iodide | 0.76 |
| Purified Water qs ad | 100 |

Iodide present in the Iodophor solution was about 0.018%. Added Iodide was 0.76%.

The resulting solution was examined for stability in Low Density Polyethylene and glass at 40° C. and Room Temperature.

EXAMPLE 12

| Ingredient | % w/v |
| --- | --- |
| PVP-I | 0.36 |
| Surfactant | 0.004 |
| Fragrance | 0.004 |
| Iodide | 0.91 |
| Purified Water qs ad | 100 |

Iodide present in the Iodophor solution was about 0.018%. Added Iodide was 0.91%.

The resulting solution was examined for stability in Low Density Polyethylene and glass at 40° C. and Room Temperature.

EXAMPLE 13

| Ingredient | % w/v |
| --- | --- |
| PVP-I | 0.36 |
| Surfactant | 0.004 |
| Fragrance | 0.004 |
| Iodide | 1.14 |
| Purified Water qs ad | 100 |

Iodide present in the Iodophor solution was about 0.018%. Added Iodide was 1.14%.

The resulting solution was examined for stability in Low Density Polyethylene and glass at 40° C. and Room Temperature.

EXAMPLE 14

| Ingredient | % w/v |
| --- | --- |
| PVP-I | 0.36 |
| Surfactant | 0.004 |
| Fragrance | 0.004 |
| Iodide | 1.52 |
| Purified Water qs ad | 100 |

Iodide present in the Iodophor solution was about 0.018%. Added Iodide was 1.52%.

The resulting solution was examined for stability in Low Density Polyethylene and glass at 40° C. and Room Temperature.

TABLE X
COMPARATIVE STABILITY DATA FOR EXAMPLES 10 TO 14 IN LOW DENSITY POLYETHYLENE AT 40° C. AND ROOM TEMPERATURE

| | % Available Iodine | | | | |
| --- | --- | --- | --- | --- | --- |
| | Example # | | | | |
| TIME | 10 | 11 | 12 | 13 | 14 |
| Initial | 0.036 | 0.036 | 0.036 | 0.036 | 0.036 |
| 1 Month/40° C. | 0.029 | 0.029 | 0.031 | 0.034 | 0.034 |
| 2 Months/40° C. | 0.025 | 0.026 | 0.036 | 0.034 | 0.034 |
| 3 Months/40° C. | 0.022 | 0.024 | 0.026 | 0.032 | 0.032 |
| 3 Month/R.T. | 0.034 | 0.033 | 0.035 | 0.035 | 0.036 |

TABLE XI
COMPARATIVE STABILITY DATA FOR EXAMPLES 10 TO 14 IN GLASS AT 40° C. AND ROOM TEMPERATURE

| | % Available Iodine | | | | |
| --- | --- | --- | --- | --- | --- |
| | Example # | | | | |
| TIME | 10 | 11 | 12 | 13 | 14 |
| Initial | 0.036 | 0.036 | 0.036 | 0.036 | 0.036 |
| 1 Month/40° C. | 0.033 | 0.033 | 0.033 | 0.034 | 0.034 |
| 2 Months/40° C. | 0.032 | 0.032 | 0.033 | 0.034 | 0.034 |
| 3 Months/40° C. | 0.032 | 0.031 | 0.032 | 0.032 | 0.032 |
| 3 Month/R.T. | 0.035 | 0.035 | 0.036 | 0.036 | 0.036 |

EXAMPLE 15

| Ingredient | % w/v |
| --- | --- |
| PVP-I | 0.6 |
| Surfactant | 0.004 |
| Fragrance | 0.004 |
| Purified Water qs ad | 100 |

Iodide present in the Iodophor solution was about 0.03%. No additional iodide was added.

The resulting solution was examined for stability in low density polyethylene at 40° C. and room temperature. In Tables XII and XIII, a comparative stability profile of Example 15 to Example 20 is presented. This series of examples demonstrates the effect of iodide on stability in the same package.

In Table XIV, comparative rabbit vaginal irritation data for Examples 15 to 20 demonstrating that the added Iodide has essentially no effect on rabbit vaginal irritation is presented.

In Table XV, comparative in vitro killing time data for Examples 15 to 20 demonstrating that the added Iodide has essentially no effect on antimicrobial activity is presented.

EXAMPLE 16

| Ingredient | % w/v |
| --- | --- |
| PVP-I | 0.6 |
| Surfactant | 0.004 |
| Fragrance | 0.004 |
| Iodide | 0.076 |
| Purified Water qs ad | 100 |

Iodide present in the Iodophor solution was about 0.03%. Added Iodide was 0.076%.

EXAMPLE 17

| Ingredient | % w/v |
| --- | --- |
| PVP-I | 0.6 |
| Surfactant | 0.004 |
| Fragrance | 0.004 |
| Iodide | 0.19 |
| Purified Water qs ad | 100 |

Iodide present in the Iodophor solution was about 0.03%. Added Iodide was 0.019%.

EXAMPLE 18

| Ingredient | % w/v |
| --- | --- |
| PVP-I | 0.6 |
| Surfactant | 0.004 |

-continued

| Ingredient | % w/v |
|---|---|
| Fragrance | 0.004 |
| Iodide | 0.38 |
| Purified Water qs ad | 100 |

Iodide present in the Iodophor solution was about 0.03%. Added Iodide was 0.038%.

EXAMPLE 19

| Ingredient | % w/v |
|---|---|
| PVP-I | 0.6 |
| Surfactant | 0.004 |
| Fragrance | 0.004 |
| Iodide | 0.57 |
| Purified Water qs ad | 100 |

Iodide present in the Iodophor solution was about 0.03%. Added Iodide was 0.056%.

EXAMPLE 20

| Ingredient | % w/v |
|---|---|
| PVP-I | 0.6 |
| Surfactant | 0.004 |
| Fragrance | 0.004 |
| Iodide | 0.76 |
| Purified Water qs ad | 100 |

Iodide present in the Iodophor solution was about 0.03%. Added Iodide was 0.076%.

TABLE XII
COMPARATIVE STABILITY DATA FOR EXAMPLES 15 TO 20 IN LOW DENSITY POLYETHYLENE AT 40° C. AND RT

| | % Available Iodine | | | | | |
|---|---|---|---|---|---|---|
| | Example # | | | | | |
| TIME | 15 | 16 | 17 | 18 | 19 | 20 |
| Initial | 0.060 | 0.059 | 0.061 | 0.059 | 0.061 | 0.059 |
| 1 Month/40° C. | 0.041 | 0.049 | 0.054 | 0.054 | 0.056 | 0.057 |
| 2 Months/40° C. | 0.025 | 0.041 | 0.048 | 0.051 | 0.053 | 0.054 |
| 3 Months/40° C. | 0.024 | 0.034 | 0.046 | 0.047 | 0.051 | 0.052 |
| 3 Month/R.T. | 0.033 | 0.057 | 0.059 | 0.058 | 0.060 | 0.060 |

TABLE XIII
COMPARATIVE STABILITY DATA FOR EXAMPLES 15 TO 20 IN GLASS AT 40° C. AND RT

| | % Available Iodine | | | | | |
|---|---|---|---|---|---|---|
| | Example # | | | | | |
| TIME | 15 | 16 | 17 | 18 | 19 | 20 |
| Initial | 0.060 | 0.059 | 0.061 | 0.059 | 0.061 | 0.059 |
| 1 Month/40° C. | 0.057 | 0.057 | 0.059 | 0.057 | 0.058 | 0.058 |
| 2 Months/40° C. | 0.056 | 0.057 | 0.058 | 0.056 | 0.057 | 0.057 |
| 3 Months/40° C. | 0.055 | 0.057 | 0.057 | 0.056 | 0.057 | 0.056 |
| 3 Month/R.T. | 0.058 | 0.059 | 0.060 | 0.057 | 0.060 | 0.060 |

TABLE XIV
RABBIT VAGINAL IRRITATION TEST FOR EXAMPLES 15 TO 20

| | Example 15 | Example 16 | Example 17 | Example 18 | Example 19 | Example 20 |
|---|---|---|---|---|---|---|
| % Iodide Inherently Contained | 0.03% | 0.03% | 0.03% | 0.03% | 0.03% | 0.03% |
| % Iodide Added | 0.0% | 0.076% | 0.19% | 0.38% | 0.57% | 0.76% |
| Rabbit Vaginal Irritation | 0/6 non-irritating | 0/6 non-irritating | 0/6 non-irritating | 0/6 non-irritating | 0/6 non-irritating | 0/6 non-irritating |

TABLE XV
In Vitro KILLING TIME TEST FOR EXAMPLES 15 TO 20

| | Example 15 | Example 16 | Example 17 | Example 18 | Example 19 | Example 20 |
|---|---|---|---|---|---|---|
| % Iodide Inherently Contained | 0.03% | 0.03% | 0.03% | 0.03% | 0.03% | 0.03% |
| % Iodide Added | 0.0% | 0.076% | 0.19% | 0.38% | 0.57% | 0.76% |
| In Vitro Killing Time | | | | | | |
| C. Albicans | <30 sec. | <30 sec | <30 sec. | 1 min. | <30 sec. | <30 sec. |
| S. Aureus | <30 sec. | <30 sec | <30 sec. | <30 sec. | <30 sec. | <30 sec. |
| G. Vaginale | <30 sec. | <30 sec | <30 sec. | <30 sec. | <30 sec. | <30 sec. |
| H. Simplex II | 1 min.* | 1 min.* | 1 min.* | 1 min.* | 1 min.* | 1 min.* |

\* ≧6 Log reduction

Thus, the comparative testing documented above, clearly illustrates the dramatic improvement in stability that is provided by the present invention herein. In particular, the percentage improvement from initial value after the addition of iodide in accordance with the present invention, is quite substantial, as illustrated below.

Referring to Example 4 (the formulation with no additional iodide included), the percent available iodine decreases from an initial value of 0.036% to 0.034% in container 1, i.e. the glass control, after 3 Mo/40° C., namely a decrease of 5.5%. However, in the case of container 3, namely the low density polyethylene form fill sealed bottle, the percent available iodine decreased from an initial value of 0.036% to 0.005%, namely a decrease in percent available iodine of 88.1%.

When considering Example 5 where 0.15% iodide was added to the iodophor formulation in accordance with the present invention, this addition did not greatly improve the stability in container 1, namely the glass container as noted in Table V, as expected. However, in all other plastic containers, a dramatic improvement in stability is documented, especially in container 3. From Table V, it is seen that the percent available iodine for container 3 has dropped from an initial level of 0.036% to 0.020%, namely a decrease in percent available iodine of only 44.4%. Typically, for PVP-I containing products, the U.S. Pharmacopeia allows a 20% overage from label claim and requires a minimum 85% of label after 3 Mo/40° C. stability testing. This translates into an allowable drop of 35%. It becomes clear then that, for container 3, although a dramatic improvement in stability has been achieved by the addition of 0.15% iodide to the formula, it is not until the added iodide is increased to 0.342% (Example 7), that the percent available iodine for container 3 will meet the U. S. Pharmacopeia guidelines.

In other words, in Example 7, the percent available iodine after 3 Mo/40° C. with respect to container 3, drops to 0.026% from an initial level of 0.036%, namely a drop of 27.7% from the initial level which is within the U. S. Pharmacopeia guidelines of maximum allowable drop of 35%

However, for containers 4 and 5, the addition of 0.15% iodide to the formula is adequate to improve stability to acceptable levels, as documented in Tables 4 and 5. For container 4, when no added iodide was included in the formula (Example 4 and Table 4), the percent average iodine dropped from 0.036% to 0.018% after 3 Mo/40° C., namely a drop of 50%. However, when 0.15% iodide was added to the formulation in accordance with the present invention in Example 5, then the percent available iodine dropped from 0.036% only to 0.031% after 3 Mo/40° C., namely a drop of only 13.9% as documented in Table V.

Similarly for container 5, the percent average iodine drops from 0.036% to 0.020% after 3 Mo/40° C. when there is no iodide added to the formula as documented in Table 4 of Example 4, namely a drop of 44.4%. With 0.15% iodide added to the formulation, the percent available iodine drops from 0.036% only to 0.031%, namely a drop of only 13.9% as documented in Table V of Example 5.

Careful examination of the testing documented below will reveal that the same trend holds for the data accumulated at conditions of elevated temperature, namely 45° C. and 56° C., but naturally with not as dramatic an improvement in stability because of these higher temperatures.

EXAMPLE 21

| Ingredient | % w/v |
|---|---|
| PVP-I | 0.36 |
| Surfactant | 0.004 |
| Fragrance | 0.004 |
| Purified Water qs ad | 100 |

Iodide present in the Iodophor solution was about 0.18%. No additional Iodide was added.

The resulting solution was examined for stability in the following packages at 56° C., and 45° C.:

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |

-continued

| PKG # | Type |
|---|---|
| 5. | High Density Polyethylene (White) |

The stability profiles at 56° C. are presented in Table XVI, and at 45° C. in Table XVII:

TABLE XVI
STABILITY PROFILE OF EXAMPLE 21 IN LDPE, HDPE AND GLASS AT 56° C.

| | % Available Iodine Package # | | | | |
|---|---|---|---|---|---|
| TIME | 1 | 2 | 3 | 4 | 5 |
| Initial | 0.036 | 0.036 | 0.036 | 0.036 | 0.036 |
| 1 Month/56° C. | 0.021 | 0.000 | 0.000 | 0.009 | 0.015 |
| 2 Months/56° C. | 0.019 | 0.000 | 0.000 | 0.001 | 0.008 |
| 3 Months/56° C. | 0.017 | 0.000 | 0.000 | 0.000 | 0.002 |

TABLE XVII
STABILITY PROFILE OF EXAMPLE 21 IN LDPE, HDPE AND GLASS AT 45° C.

| | % Available Iodine Package # | | | | |
|---|---|---|---|---|---|
| TIME | 1 | 2 | 3 | 4 | 5 |
| Initial | 0.036 | 0.036 | 0.036 | 0.036 | 0.036 |
| 1 Month/45° C. | 0.032 | 0.008 | 0.000 | 0.023 | 0.025 |
| 2 Months/45° C. | 0.030 | 0.008 | 0.000 | 0.016 | 0.018 |
| 3 Months/45° C. | 0.028 | 0.000 | 0.000 | 0.011 | 0.011 |

EXAMPLE 22

| Ingredient | % w/v |
|---|---|
| PVP-I | 0.36 |
| Surfactant | 0.004 |
| Fragrance | 0.004 |
| Iodide | 0.15 |
| Purified Water qs ad | 100 |

Iodide present in the Iodophor solution was about 0.18%. Added Iodide was 0.15%.

The resulting solution was examined for stability in the following packages at 56° C., and 45° C.:

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

The stability profiles at 56° C. are presented in Table XVIII, and at 45° C. in Table XIX:

TABLE XVIII
STABILITY PROFILE OF EXAMPLE 22 IN LDPE, HDPE AND GLASS AT 56° C.

| | % Available Iodine Package # | | | | |
|---|---|---|---|---|---|
| TIME | 1 | 2 | 3 | 4 | 5 |
| Initial | 0.036 | 0.036 | 0.036 | 0.036 | 0.036 |
| 1 Month/56° C. | 0.031 | 0.013 | 0.000 | 0.025 | 0.026 |
| 2 Months/56° C. | 0.030 | 0.004 | 0.000 | 0.019 | 0.021 |
| 3 Months/56° C. | 0.029 | 0.001 | 0.000 | 0.011 | 0.019 |

TABLE XIX

STABILITY PROFILE OF EXAMPLE 22 IN LDPE, HDPE AND GLASS AT 45° C.

| | % Available Iodine | | | | |
|---|---|---|---|---|---|
| | Package # | | | | |
| TIME | 1 | 2 | 3 | 4 | 5 |
| Initial | 0.036 | 0.036 | 0.036 | 0.036 | 0.036 |
| 1 Month/45° C. | 0.034 | 0.028 | 0.026 | 0.032 | 0.031 |
| 2 Months/45° C. | 0.032 | 0.023 | 0.020 | 0.030 | 0.030 |
| 3 Months/45° C. | 0.032 | 0.020 | 0.017 | 0.030 | 0.029 |

EXAMPLE 23

| Ingredient | % w/v |
|---|---|
| PVP-I | 0.36 |
| Surfactant | 0.004 |
| Fragrance | 0.004 |
| Iodide | 0.228 |
| Purified Water qs ad | 100 |

Iodide present in the Iodophor solution was about 0.18%. Added Iodide was 0.228%.

The resulting solution was examined for stability in the following packages at 56° C., and 45° C.

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

The stability profiles at 56° C. are presented in Table XX, and at 45° C. in Table XXI:

TABLE XX

STABILITY PROFILE OF EXAMPLE 23 IN LDPE, HDPE AND GLASS AT 56° C.

| | % Available Iodine | | | | |
|---|---|---|---|---|---|
| | Package # | | | | |
| TIME | 1 | 2 | 3 | 4 | 5 |
| Initial | 0.036 | 0.036 | 0.036 | 0.036 | 0.036 |
| 1 Month/56° C. | 0.032 | 0.022 | 0.010 | 0.028 | 0.030 |
| 2 Months/56° C. | 0.031 | 0.011 | 0.000 | 0.023 | 0.027 |
| 3 Months/56° C. | 0.030 | 0.009 | 0.500 | 0.020 | 0.023 |

TABLE XXI

STABILITY PROFILE OF EXAMPLE 23 IN LDPE, HDPE AND GLASS AT 45° C.

| | % Available Iodine | | | | |
|---|---|---|---|---|---|
| | Package # | | | | |
| TIME | 1 | 2 | 3 | 4 | 5 |
| Initial | 0.036 | 0.036 | 0.036 | 0.036 | 0.036 |
| 1 Month/45° C. | 0.036 | 0.030 | 0.029 | 0.033 | 0.032 |
| 2 Months/45° C. | 0.034 | 0.026 | 0.025 | 0.031 | 0.015 |
| 3 Months/45° C. | 0.034 | 0.024 | 0.019 | 0.030 | 0.030 |

EXAMPLE 24

| Ingredient | % w/v |
|---|---|
| PVP-I | 0.36 |
| Surfactant | 0.004 |
| Fragrance | 0.004 |
| Iodide | 0.342 |
| Purified Water qs ad | 100 |

Iodide present in the Iodophor solution was about 0.18%. Added Iodide was 0.342%.

The resulting solution was examined for stability in the following packages at 56° C., and 45° C.

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

The stability profiles at 56° C. are presented in Table XXII, and at 45° C. in Table XXIII:

TABLE XXII

STABILITY PROFILE OF EXAMPLE 24 IN LDPE, HDPE AND GLASS AT 56° C.

| | % Available Iodine | | | | |
|---|---|---|---|---|---|
| | Package # | | | | |
| TIME | 1 | 2 | 3 | 4 | 5 |
| Initial | 0.036 | 0.036 | 0.036 | 0.036 | 0.036 |
| 1 Month/56° C. | 0.032 | 0.026 | 0.019 | 0.030 | 0.032 |
| 2 Months/56° C. | 0.032 | 0.016 | — | 0.027 | 0.028 |
| 3 Months/56° C. | 0.031 | 0.013 | — | 0.024 | 0.025 |

TABLE XXIII

STABILITY PROFILE OF EXAMPLE 24 IN LDPE, HDPE AND GLASS AT 45° C.

| | % Available Iodine | | | | |
|---|---|---|---|---|---|
| | Package # | | | | |
| TIME | 1 | 2 | 3 | 4 | 5 |
| Initial | 0.036 | 0.036 | 0.036 | 0.036 | 0.036 |
| 1 Month/45° C. | 0.036 | 0.032 | 0.030 | 0.034 | 0.036 |
| 2 Months/45° C. | 0.035 | 0.031 | 0.028 | 0.031 | 0.031 |
| 3 Months/45° C. | 0.034 | 0.027 | 0.025 | 0.032 | 0.030 |

EXAMPLE 25

| Ingredient | % w/v |
|---|---|
| PVP-I | 0.45 |
| Surfactant | 0.004 |
| Fragrance | 0.004 |
| Iodide | 0.285 |
| Purified Water qs ad | 100 |

Iodide present in the Iodophor solution was about 0.023%. Added Iodide was 0.285%.

The resulting solution was examined for stability in the following packages at 56° C., and 45° C.

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

The stability profiles at 56° C. are presented in Table XXIV, and at 45° C. in Table XXV:

TABLE XXIV
STABILITY PROFILE OF EXAMPLE 25 IN LDPE, HDPE AND GLASS AT 56° C.
% Available Iodine

| TIME | Package # 1 | 2 | 3 | 4 | 5 |
|---|---|---|---|---|---|
| Initial | 0.045 | 0.045 | 0.045 | 0.045 | 0.045 |
| 1 Month/56° C. | 0.041 | 0.028 | 0.021 | 0.038 | 0.037 |
| 2 Months/56° C. | 0.040 | 0.018 | — | 0.033 | 0.034 |
| 3 Months/56° C. | 0.040 | 0.010 | — | 0.029 | 0.030 |

TABLE XXV
STABILITY PROFILE OF EXAMPLE 25 IN LDPE, HDPE AND GLASS AT 45° C.
% Available Iodine

| TIME | Package # 1 | 2 | 3 | 4 | 5 |
|---|---|---|---|---|---|
| Initial | 0.045 | 0.045 | 0.045 | 0.045 | 0.045 |
| 1 Month/45° C. | 0.044 | 0.040 | 0.038 | 0.042 | 0.042 |
| 2 Months/45° C. | 0.043 | 0.037 | 0.035 | 0.041 | 0.040 |
| 3 Months/45° C. | 0.042 | 0.034 | 0.032 | 0.040 | 0.039 |

EXAMPLE 26

| Ingredient | % w/v |
|---|---|
| PVP-I | 0.45 |
| Surfactant | 0.004 |
| Fragrance | 0.004 |
| Iodide | 0.426 |
| Purified Water qs ad | 100 |
| Iodide present in the Iodophor solution was about 0.022%. | |
| Added Iodide was 0.426%. | |

The resulting solution was examined for stability in the following packages at 56° C., and 45° C.

| PKG # | Type |
|---|---|
| 1. | Glass |
| 2. | Low Density Polyethylene |
| 3. | Low Density Polyethylene form fill seal bottle. |
| 4. | High Density Polyethylene (Natural) |
| 5. | High Density Polyethylene (White) |

The stability profiles at 56° C. are presented in Table XXVI, and at 45° C. in Table XXVII:

TABLE XXVI
STABILITY PROFILE OF EXAMPLE 26 IN LDPE, HDPE AND GLASS AT 56° C.
% Available Iodine

| TIME | Package # 1 | 2 | 3 | 4 | 5 |
|---|---|---|---|---|---|
| Initial | 0.045 | 0.045 | 0.045 | 0.045 | 0.045 |
| 1 Month/56° C. | 0.041 | 0.036 | 0.028 | 0.040 | 0.040 |
| 2 Months/56° C. | 0.040 | 0.027 | — | 0.036 | 0.039 |
| 3 Months/56° C. | 0.040 | 0.020 | — | 0.033 | 0.036 |

TABLE XXVII
STABILITY PROFILE OF EXAMPLE 26 IN LDPE, HDPE AND GLASS AT 45° C.
% Available Iodine

| TIME | Package # 1 | 2 | 3 | 4 | 5 |
|---|---|---|---|---|---|
| Initial | 0.045 | 0.045 | 0.045 | 0.045 | 0.045 |
| 1 Month/45° C. | 0.044 | 0.041 | 0.041 | 0.043 | 0.042 |
| 2 Months/45° C. | 0.044 | 0.038 | 0.036 | 0.041 | 0.041 |
| 3 Months/45° C. | 0.043 | 0.036 | 0.034 | 0.041 | 0.040 |

While it is clear that prevention of leaching of iodine occurs when the package is plastic, the improvement in stability when the packaging in non-permeable (glass) is also documented. For example, considering examples 21, 22, and 23, example 21 contains no additional iodide added, example 22 contains 0.15% additional iodide added, and example 23 contains 0.228% additional iodide added. When the stability at 56° C. (Table XVI, XVIII, XX) in glass (a material which is non-permeable to iodine) is examined, an observed improvement in stability which added iodide is documented below in Table XXVIII:

TABLE XXVIII

| Added Iodide | Example 21 None Glass | Example 22 0.15% % Available Iodine (w/v) Package (#1) Glass | Example 23 0.228% Glass |
|---|---|---|---|
| Initial | 0.036 | 0.036 | 0.036 |
| 1 Month/56° C. | 0.021 | 0.031 | 0.032 |
| 2 Month/56° C. | 0.019 | 0.030 | 0.031 |
| 3 Month/56° C. | 0.017 | 0.029 | 0.030 |
| | | An improvement in stability at 3 MO/56° C. of 33.3% over Example 21 | At 3 MO/56° C. an improvement in stability of 36% over Ex. 21 |

Although the examples above relate to liquid products, other dosage forms (such as semi-solids) will also show stabilization of iodophor and prevention of leaking of iodine through packaging with the added iodide.

The preceding description of the present invention is merely exemplary, and is not intended to limit the scope thereof in any way.

What is claimed is:

1. A stable packaged iodophor solution comprising polyethylene walled container through which walls, iodine from the iodophor solutions containing iodide ions leach in a maximum amount of up to 6.6% according to U.S. Pharmacopeia XXII, said container containing a microbicidal effective iodophor solution containing iodide ions in an amount greater than said U.S. Pharmacopeia maximum amount of 6.6% and sufficient to minimize leaching of iodine from said iodophor solution through the walls of said container.

2. A packaged iodophor solution according to claim 1, wherein said iodide ions sufficient to minimize leaching of the iodine from said iodophor solution is obtained by the addition of an iodide to said solution.

3. The packaged iodophor solution of claim 1, wherein the iodophor is polyvinyl pyrrolidone.

4. The packaged iodophor solution of claim 1, wherein said container is formed from polyethylene.

5. The packaged iodophor solution of claim 1, wherein said container is a sealed plastic container.

6. The packaged iodophor solution of claim 5 wherein said container is a plastic douche bottle.

7. The packaged iodophor solution of claim 2, wherein said solution contains at least about 0.01% by weight of the additional iodide, based on the iodophor solution.

8. The packaged iodophor solution of claim 7, containing up to about 4.0% of the additional iodide.

9. The packaged iodophor solution of claim 8, containing up to about 1.5% of the additional iodide.

10. The packaged iodophor solution of claim 9, containing up to about 1.0% of the additional iodide.

11. The packaged iodophor solution of claim 10, containing up to about 0.2% of the additional iodide.

12. The packaged iodophor solution of claim 11, containing up to about 0.07% of the additional iodide.

13. The packaged iodophor solution of claim 12, wherein the iodophor solution comprises about 0.01%–0.3% of iodine therein, in addition to said additional amount of iodide.

14. The packaged iodophor solution of claim 2 wherein said additional iodide is obtained from KI.

* * * * *